US008541443B2

(12) United States Patent
Suzuki et al.

(10) Patent No.: US 8,541,443 B2
(45) Date of Patent: Sep. 24, 2013

(54) CRYSTAL OF DIAMINE DERIVATIVE AND METHOD OF PRODUCING SAME

(71) Applicant: Daiichi Sankyo Company, Limited, Tokyo (JP)

(72) Inventors: Tetsuya Suzuki, Tokyo (JP); Makoto Ono, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/622,783

(22) Filed: Sep. 19, 2012

(65) Prior Publication Data
US 2013/0035356 A1 Feb. 7, 2013

Related U.S. Application Data

(63) Continuation of application No. PCT/JP2011/055955, filed on Mar. 14, 2011.

(30) Foreign Application Priority Data
Mar. 19, 2010 (JP) ................................. 2010-063693

(51) Int. Cl.
A61K 31/44 (2006.01)
(52) U.S. Cl.
USPC ........................................................ 514/301
(58) Field of Classification Search
USPC ........................................................ 514/301
See application file for complete search history.

(56) References Cited

U.S. PATENT DOCUMENTS

| 5,055,600 | A | 10/1991 | Wagner |
| 5,149,855 | A | 9/1992 | Sakimae et al. |
| 5,677,469 | A | 10/1997 | van Eikeren et al. |
| 7,192,968 | B2 | 3/2007 | Yoshino et al. |
| 7,342,014 | B2 | 3/2008 | Ohta et al. |
| 7,365,205 | B2 | 4/2008 | Ohta et al. |
| 7,576,135 | B2 | 8/2009 | Ohta et al. |
| 7,674,904 | B2 | 3/2010 | Doshan et al. |
| 2004/0122063 | A1 | 6/2004 | Yoshino et al. |
| 2005/0020645 | A1 | 1/2005 | Ohta et al. |
| 2005/0119486 | A1 | 6/2005 | Ohta et al. |
| 2005/0245565 | A1 | 11/2005 | Ohta et al. |
| 2006/0252837 | A1 | 11/2006 | Ohta et al. |
| 2006/0275357 | A1 | 12/2006 | Oomura et al. |
| 2007/0135476 | A1 | 6/2007 | Nagasawa et al. |
| 2008/0015215 | A1 | 1/2008 | Ohta et al. |
| 2009/0105491 | A1 | 4/2009 | Sato et al. |
| 2009/0192313 | A1 | 7/2009 | Nagasawa et al. |
| 2009/0270446 | A1 | 10/2009 | Ohta et al. |
| 2009/0281074 | A1 | 11/2009 | Ohta et al. |
| 2010/0081685 | A1 | 4/2010 | Kojima et al. |

FOREIGN PATENT DOCUMENTS

| JP | 4-227629 | 8/1992 |
| JP | 11-180899 | 7/1999 |
| JP | 2000-344735 | 12/2000 |
| JP | 2001-151724 | 6/2001 |
| JP | 2008-542287 | 11/2008 |
| JP | 2010-254615 | 11/2010 |
| WO | 01/74774 | 10/2001 |
| WO | 03/000657 | 1/2003 |
| WO | 03/000680 | 1/2003 |
| WO | 03/016302 | 2/2003 |
| WO | 2004/058715 | 7/2004 |
| WO | 2005/047296 | 5/2005 |
| WO | 2007/032498 | 3/2007 |
| WO | 2008/129846 | 10/2008 |
| WO | 2008/156159 | 12/2008 |
| WO | 2010/021093 | 2/2010 |
| WO | 2010/071164 | 6/2010 |

OTHER PUBLICATIONS

U.S. Appl. No. 13/157,590, filed Jun. 10, 2011, Koji Sato.
U.S. Appl. No. 13/162,922, filed Jun. 17, 2011, Takeo Koyama.
U.S. Appl. No. 13/163,287, filed Jun. 17, 2011, Takashi Abiko.
U.S. Appl. No. 13/181,596, filed Jul. 13, 2011, Makoto Ono.
U.S. Appl. No. 13/273,360, filed Oct. 14, 2011, Toshiharu Yoshino.
U.S. Appl. No. 13/328,847, filed Dec. 16, 2011, Makoto Kamada.
U.S. Appl. No. 13/554,610, filed Jul. 20, 2012, Tetsuya Kimura.
U.S. Appl. No. 13/732,857, filed Jan. 2, 2013, Koutarou Kawanami.
U.S. Appl. No. 13/231,081, filed Sep. 2, 2011, Koutarou Kawanami.
U.S. Appl. No. 13/228,928, filed Sep. 9, 2011, Takeo Koyama.
De La Mode et al. "Effect of Renal Function on Edoxaban Pharamacokinetics (PK) and on population PK/PK-PD model" Journal of Clinical Pharmacology, 49(9), p. 1124, 2009, abstract only.
Instruction Manual of the Japanese Pharmacopoeia, 15th et, 2006, B-211 to B-217.
Weitz, J. I. et al. (2010). "Randomised, parallel-group, multicentre, multinational phase 2 study comparing edoxaban, an oral factor Xa inhibitor, with warfarin for stroke prevention in patients with atrial fibrillation". Thrombosis and Haemostasis 104 (3): 633-641.
Ruff C.T. et al. "Evaluation of the novel factor Xa inhibitor edoxaban compared with warfarin in patients with atrial fibrillation: Design and rationale for the Effective aNticoaGulation with factor xA next GEneration in Atrial Fibrillation—Thrombolysis in Myocardial Infarction study 48 (ENGAGE AF—TIMI 48)" Am. Heart J. Oct. 2010; 160 (4): 635-41.
Lixiana (registered trademark) tablets, package insert, the 2nd revised edition in Jul. 2011.
Homepage of information on ethical pharmaceuticals review (http://www.info.pmda.go.jp/approvalSrch/PharmacySrchInit?), Pharmaceuticals and Medical Devices Agency, LIXIANA (registered trademark) tablets, The Brief Summary of Application Material, 2.7.6 Summary of Individual Studies, 114-128.
Homepage of information on ethical pharmaceuticals review (http://www.info.pmda.go.jp/approvalSrch/PharmacySrchInit?), Pharmaceuticals and Medical Devices Agency, LIXIANA (registered trademark) tablets, The Brief Summary of Application Material, 2.5 Global Assessment for Clinical Practice 48-76.

(Continued)

Primary Examiner — Brandon Fetterolf
Assistant Examiner — Christopher R Stone
(74) Attorney, Agent, or Firm — Locke Lord LLP

(57) ABSTRACT

An object of the present invention is to provide a novel crystal form of a compound that has an inhibitory effect on activated blood coagulation factor X and is useful as a pharmaceutical compound for prevention and/or treatment of thrombotic and/or embolic diseases. The present invention provides a novel crystal form of $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate monohydrate, and method for producing the same.

22 Claims, 10 Drawing Sheets

(56) References Cited

OTHER PUBLICATIONS

Homepage of information on ethical pharmaceuticals review (http://www.info.pmda.go.jp/approvalSrch/PharmacySrchlnit?), Pharmaceuticals and Medical Devices Agency, LIXIANA (registered trademark) tablets, The Brief Summary of Application Material, 2.7.2 Clinical Pharmacological Study, 30-32 Section "2.3.2 PK for Renal Functional Impairment in Europe".

Assessment Report as of Feb. 9, 2011 for LIXIANA (registered trademark) tablets, 41-43 Section "(2) Validity of Reduced Dose for Renal Functional Impairment Patient and for combined use with P-gp inhibitor".

Assessment Report as of Feb. 9, 2011 for LIXIANA (registered trademark) tablets, 66-69 Section "(7)1 Individual with Renal Functional Impairment".

Assessment Report as of Feb. 9, 2011 for LIXIANA (registered trademark) tablets, 74-78.

Ogawa, S. et al. "Antithrombotic therapy in atrial fibrillation: evaluation and positioning of new oral anticoagulant agents", Circ. J., 2011, vol. 75, 1539-1547.

Serajuddin, Abu T.M. "Salt formation to improve drug solubility", Advanced Drug Delivery Reviews 59 (2007), 603-616.

Dubois, D., et al., "Clinical calorimetry. X. A formula to estimate the approximate surface area if the height and weight be known" Archives of Internal Medicine, 17, 863-71 (1916).

Elodi, S., et al., "Optimization of conditions for the catalytic effect of the factor IXa-factor VIII complex: probable role of the complex in the amplification of blood coagulation" Thrombosis Research, 15(5-6), 617-29 (1979).

Fujimoto, et al., "Studies on the physical surface area of Japanese: Part 18 calculation formulas in three stages over all age" Japanese Journal of Hygene, vol. 23(5): 443-450 (1968)—(Contains an English Abstract).

Furugohri, T., et al., "DU-176b, A potent and orally active factor Xa inhibitor: In vitro and in vivo pharmacological profiles" Journal of Thrombosis and Haemostasis, 6(9), 1542-1549 (2008).

Goldberg, Si, et al., "Correlation of configuration and rotatory direction for several 4-substituted cyclohexenes" Journal of Organic Chemistry, 31:240-243 (1966).

Hylek, E.M., "Drug evaluation: DU-176b, an oral, direct Factor Xa antagonist." Current Opinion in Investigational Drugs, 8, (9), 778-783 (2007).

Johansson, LC, et al., "Comparison of the Pharmacokinetics and Pharacodynamics of Ximelagatran in young and elderly, healthy Japanese men" Blood 100, 3980 (2002).

Mendell, J., et al., "The pharmacokinetics and pharmacodynamics of the direct factor Xa inhibitor, edoxaban co-administered with digoxin: a randomized, open-label, dual treatment sequence, parallel-group study" Journal of Clinical Pharmacology, 49(9), 1125 (2009).

Mendell, J., et al., "Thorough QT/QTC study with edoxaban to evaluate effect of therapeutic and supratherapeutic exposure on QTC interval duration in healthy subjects" Journal of Clinical pharmacology 49(9), 1122 (2009).

Mould, D., et al., "A population pharmacokinetic pharmacodynamic and logistic regression analysis of lotrafiban in patients" Clinical Pharmacology and Therapeutics 69(4), 210-222 (2001).

Mueck, W., et al., "Population pharmacokinetics and pharmacodynamic of rivaroxaban—an oral, direct factor Xa inhibitor—in patients undergoing major orthopaedic surgery" Clinical Pharmacokinetics, 47(3), 203-216 (2008).

Nohira, H. "4 Diastereomer Method", Edited by CSJ: The Chemical Society of Japan, kogaku Iseitai no Bunri Kikan Kagaku Sosetsu No. 6, 3rd edition, Japan Scientific Societies Press, pp. 45 to 54, (1999). Product Information, Clexane® and Clexane® Forte, Clexane® PI MKT, #6178v16, pp. 1-19 (2008).

Ridout, G., et al., "Effect of renal function on edoxaban pharmacokinetics (PK) and on population PK/PK-PD model" Journal of Clinical Pharmcology 49(9), 1124 (2009).

Schwartz, HM, et al., "Predicting the Enantiomeric Selectivity of Chymotrypsin. Homologous Series of Ester Substrates" J. Am. Chem. Soc., 100, 5199-5203, (1978).

Sixma JJ, et al., "The ideal anti-thrombotic drug" Thrombosis research, 68(6), 507-12 (1992).

Takahashi, H. "3.Warfarin Oto no kojinsa" Kessen to Junkan, 14(3), 198-202 (2006) (English Translation Provided).

Tanyeli, C, et al., "Enzyme catalyzed reverse enantiomeric separation of methyl (±)-3-cyclohexene-1-carboxylate" Tetrahedron: Asymmetry, 15, 2057-2060, (2004).

Trost, BM, et al., "An Asymmetric Synthesis of (+)-Phyllanthoci" Tetrahedron Lett., 32, 1613-1616, (1991).

Vene, N., et al., "High D-dimer levels predict cardiovascular events in patients with chronic atrial fibrillation during oral anticoagulant therapy" Thrombosis and Haemostasis, 90(6), 1163-1172 (2003).

Kozma, D., "CRC Handbook of Optical Resolutions Via Diastereomeric Salt Formation", CRC Press: Washington, DC, Chapters 4, 5, and 6 (2002).

Murakami, "Asymmetric Transformation of a Racemic a-(Phthalimidooxy)arylacetic Ester by a Combination of Preferential Crystallization and Simultaneous Racemization" Chirality 5141-48 (1993).

Allan, R., "Synthesis of analogs of GABA. VI. Stereoisomers of cis-3-aminocyclohexanecarboxylic acid" Australian Journal of Chemistry, 34(10):2231-36 (Abstract only).

Chiappe, et al. "Nucleophilic Displacement Reactions in Ionic Liquids: Substrate and Solvent Effect in the Reaction of NaN3 and KCN with Alkyl Halides and Tosylates," Journal of Organic Chemistry 68:6710-15 (2003).

Betti, C., et al. "Reactivity of anionic nucleophiles in ionic liquids and molecular solvents," Tetrahedron 64:1689 (2008).

Blagden, N., et al. "Crystal engineering of active pharmaceutical ingredients to improve solubility and dissolution rates." Advanced Drug Delivery Reviews, 59:603-616 (2007).

Serajuddin, A., "Salt formation to improve drug solubility." Advanced Drug Delivery Reviews, 59:617-630 (2007).

Ohta, T. et al. "Preparation of N,N'-bis(heterocyclic acyl)cycloalkanediamine and heterocyclediamine derivatives as inhibitors of activated blood coagulation factor X (factor Xa)", Hcaplus 2003:5928 (2003).

Furugohri, T, et al, "Pharmaceutical Characterization, Antithromboti and Bleeding Effects of DU-176b", Journal of Thrombosis and Haemostasis, 3(supp. 1), Abstract P1110, (2005).

Zafar, UM, et al., "Antithrombotic effects of factor Xa inhibition with DU-176b: Phase-I study of an oral, direct factor Xa inhibitor using an ex-vivo flow chamber", Thrombosis and Haemostasis, 98(4):833-888 (2007).

Walker, MB, "Understanding the PT-INR Test", obtained from the internet www.vclotacare.com/ptinr.aspx (retrieved Apr. 24, 2012).

Anonymous, "A phase 2, randomized, parallel group, multi-center, multi-national study for the evaluation of safety and efficacy of two fixed dosages of DU-176b in subjects with non-valvular atrial fibrillation", Clinical Trials.gov NCT00806624 obtained from the internet clinicaltrials.gov/archive/NCT00806624/2008_12_10 (retrieved Apr. 23, 2012).

Hyers, T. M., et al, "Management of Venous Thromboembolism", Arch Intern Med., 163:759-768 (2003).

Turpie, Agg., "Oral, direct factor Xa inhibitors in development for the prevention and treatment of thromboembolic diseases", Arteriosclerosis, Thrombosis, and Vascular Biology, 27:1238-1247 (2007).

De Caterina, R, et al. "Anticoagulants in heart disease: current status and perspectives", European Heart Journal 28:880-913 (2007).

Dyke, CK, "First experience with direct factor Xa inhibition in patients with stable coronary disease: a pharmacokinetic and pharmacodynamics evaluation", Circulation., 105:2385-2391 (2002).

Iba, T., et al., "Factor Xa-inhibitor (DX-9065a) modulates the leukocyte-endothelial cell interaction in endotoxemic rat", Shock., 17(2):159-162 (2002).

Escolar et al. "Edoxaban tosilate: Direct factor Xa inhibitor prevention of post operative venous thromboembolism treatment of atrial fibrillation" Drugs of the Future, 34(11), p. 861-872, 2009, Abstract only.

International Preliminary Report on Patentability, issued in PCT/JP2009/070613, mailed Jul. 5, 2011.
International Search Report, issued in PCT/JP2009/070613, mailed Feb. 16, 2010.
Written Opinion of the International Searching Authority, issued in PCT/JP2009/070613, mailed Jul. 5, 2011.
International Preliminary Report on Patentability, issued in PCT/JP2009/070874, mailed Jul. 5, 2011.
International Search Report, issued in PCT/JP2009/070874, mailed Mar. 23, 2010.
Written Opinion of the International Searching Authority, issued in PCT/JP2009/070874, mailed Jul. 5, 2011.
International Preliminary Report on Patentability, issued in PCT/JP2009/071016, mailed Jul. 5, 2011.
International Search Report, issued in PCT/JP2009/071016, mailed Feb. 16, 2010.
Written Opinion of the International Searching Authority, issued in PCT/JP2009/071016, mailed Jul. 5, 2011.
International Preliminary Report on Patentability, issued in PCT/JP2010/050128, mailed Aug. 16, 2011.
International Search Report, issued in PCT/JP2010/050128, mailed Apr. 6, 2010.
Written Opinion of the International Searching Authority, issued in PCT/JP2010/050128, mailed Aug. 16, 2011.
International Preliminary Report on Patentability, issued in PCT/JP2010/057990, mailed Dec. 12, 2011.
International Search Report, issued in PCT/JP2010/057990, mailed Jun. 8, 2010.
Written Opinion of the International Searching Authority, issued in PCT/JP2010/057990, mailed Dec. 12, 2011.
International Preliminary Report on Patentability, issued in PCT/JP2010/060261, mailed Dec. 20, 2011.
International Search Report, issued in PCT/JP2010/060261, mailed Sep. 21, 2010.
Written Opinion of the International Searching Authority, issued in PCT/JP2010/060261, mailed Dec. 20, 2011.
PCT International Preliminary Report on Patentability of Int'l App. No. PCT/JP2010/053905 dated Oct. 18, 2011, 5 pages.
International Search Report of Int'l App. No. PCT/JP2010/053905 dated Apr. 21, 2010, 2 pages.
English Translation of PCT Written Opinion of the International Searching Authority of Int'l App. No. PCT/JP2010/053905 dated May 11, 2010, 4 pages.
PCT International Preliminary Report on Patentability of Int'l App. No. PCT/JP2010/053976 dated Oct. 18, 2011, 5 pages.
International Search Report of Int'l App. No. PCT/JP2010/053976 dated Apr. 13, 2010, 2 pages.
English Translation of PCT Written Opinion of the International Searching Authority of Int'l App. No. PCT/JP2010/053976 dated Apr. 13, 2010, 4 pages.
Patani, et al., "Bioisosterism: A rational approach in drug design", Chem. Rev. 1996, 3147-3176.
International Search Report of Int'l App. No. PCT/JP2011/065192 dated Jan. 5, 2012.
Written Opinion of the International Search Authority of Int'l App. No. PCT/JP2011/065192 dated Feb. 6, 2013.
International Preliminary Report on Patentability Chapter I (IB/373) of Int'l App. No. PCT/JP2011/065192 dated Feb. 12, 2013.
Extended European Search Report dated Jul. 3, 2013 issued in corresponding European Application No. EP 11756251.2.

| Solvent | S/B RATIO | Crystal form |
|---|---|---|
| Acetonitrile | 7.9 | Form II |
| Water | 5.4 | Low crystalline |
| Ethanol | 23.6 | Form I |

Figure 4

| 2θ (°) | d value (Å) | Relative intensity (%) |
|---|---|---|
| 5.4±0.2 | 16.31 | 37.2 |
| 12.8±0.2 | 6.91 | 36.0 |
| 13.9±0.2 | 6.37 | 24.8 |
| 14.2±0.2 | 6.23 | 32.3 |
| 15.8±0.2 | 5.61 | 28.8 |
| 16.2±0.2 | 5.45 | 44.6 |
| 17.1±0.2 | 5.18 | 79.9 |
| 17.2±0.2 | 5.15 | 95.0 |
| 17.5±0.2 | 5.07 | 81.3 |
| 18.2±0.2 | 4.88 | 41.5 |
| 20.7±0.2 | 4.28 | 83.9 |
| 21.5±0.2 | 4.14 | 100.0 |
| 22.0±0.2 | 4.05 | 43.5 |
| 22.3±0.2 | 3.98 | 83.5 |
| 22.6±0.2 | 3.94 | 54.3 |
| 23.2±0.2 | 3.83 | 85.9 |
| 24.3±0.2 | 3.66 | 43.8 |
| 26.2±0.2 | 3.40 | 39.9 |
| 27.2±0.2 | 3.27 | 46.4 |

Figure 7

| Absorption band (cm-1) | Assignment | Intensity |
|---|---|---|
| 3600-3200 | O-H stretching vibration | Weak |
| 3353±5 3313±5 | N-H stretching vibration, O-H stretching vibration | Moderate |
| 3100-2900 | C-H stretching vibration | Weak |
| 2700-2500 | N-H stretching vibration | Weak |
| 1675±2 | C=O stretching vibration | Strong |
| 1614±2 | C=O stretching vibration | Strong |
| 1505±2 | C=C stretching vibration | Strong |
| 1222±1 | S=O asymmetric stretching vibration | Strong |
| 1172±1 | S=O asymmetric stretching vibration | Strong |
| 839±1 | C-H out-of-plane bending | Moderate |
| 828±1 | C-H out-of-plane bending | Moderate |

CRYSTAL OF DIAMINE DERIVATIVE AND METHOD OF PRODUCING SAME

This application is a continuation of International Application No. PCT/JP2011/055955, filed on Mar. 14, 2011, entitled "CRYSTAL OF DIAMINE DERIVATIVE AND METHOD OF PRODUCING SAME", which claims the benefit of Japanese Patent Application Number JP 2010-063693, filed on Mar. 19, 2010, both of which are hereby incorporated by reference.

FIELD OF THE INVENTION

The present invention relates to crystals of a compound that exhibits an inhibitory effect on activated blood coagulation factor X (FXa) and is useful as an agent for preventing and/or treating thrombotic diseases.

BACKGROUND $N^1$-(5-chloropyridin-2-yl)-$N^2$-((1S, 2R, 4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate monohydrate represented by the following formula (I) (in the present specification, also referred to as compound I):

[Formula 1]

(I)

is known as a compound that exhibits an inhibitory effect on activated blood coagulation factor X (FXa) and is useful as a preventive and/or therapeutic drug for thrombotic diseases (Patent Documents 1 to 9). Crystals described in Patent Document 9 (in the present specification, also referred to as "Form I crystals of compound I" or "Form I crystals") are known as crystals of compound I.

CITATION LIST

Patent Document

Patent Document 1: WO03/000657
Patent Document 2: WO03/000680
Patent Document 3: WO03/016302
Patent Document 4: WO04/058715
Patent Document 5: WO05/047296
Patent Document 6: WO07/032498
Patent Document 7: WO08/129846
Patent Document 8: WO08/156159
Patent Document 9: Japanese Patent Laid-Open No. 2010-254615

SUMMARY OF THE INVENTION

Technical Problem

An object of the present invention is to provide novel crystals of compound I.

Solution to Problem

In an attempt to acquire novel crystals of compound I, the present inventors have failed to reproducibly and stably obtain novel crystals of compound I, even under varying crystallization conditions in slurry stirring or recrystallization methods usually used for crystal polymorph searches. However, as a result of trial and error, the present inventors have found that novel crystals (in the present specification, also referred to as "Form II crystals of compound I" or "Form II crystals"; the terms "Form II crystals of compound I" and "Form II crystals" are interchangeably used in the present specification) can be obtained reproducibly and stably only under special conditions involving temporarily converting compound I to an amorphous or low crystalline solid and exposing the amorphous or low crystalline solid to solvent vapor. Based on this finding, the present invention has been completed.

Specifically, the present invention relates to the following:
[1] Form II crystals of compound I comprising a peak at a diffraction angle (2θ) of 22.3±0.2 or 23.2±0.2(°) in powder x-ray diffraction obtained using Cu-Kα rays;
[2] the crystals according to [1], comprising peaks at diffraction angles (2θ) of 22.3±0.2 and 23.2±0.2(°) in powder x-ray diffraction obtained using Cu-Kα rays;
[3] the crystals according to [1], further comprising a peak at a diffraction angle (2θ) of 21.5±0.2 or 22.0±0.2(°) in powder x-ray diffraction obtained using Cu-Kα rays;
[4] the crystals according to [1], comprising peaks at diffraction angles (2θ) of 13.9±0.2, 14.2±0.2, 15.8±0.2, 16.2±0.2, 18.2±0.2, 21.5±0.2, 22.0±0.2, 22.3±0.2, 23.2±0.2, and 24.3±0.2(°) in powder x-ray diffraction obtained using Cu-Kα rays;
[5] the crystals according to [1], wherein the powder x-ray diffraction obtained using Cu-Kα rays shows a pattern represented by (2) of FIG. 1(a) or FIG. 3;
[6] the crystals according to [1], wherein the crystals exhibit a differential thermal analysis (DTA) profile having at least one endothermic peak in any one of the ranges of 160° C. to 170° C. and 215° C. to 225° C.;

[7] the crystals according to [1], comprising any one absorption band selected from the group consisting of 3313±5, 839±1, and 828±1 (cm$^{-1}$) in a Fourier-transform infrared absorption spectrum pattern;

[8] the crystals according to [1], wherein the crystals have at least one feature selected from the group consisting of the following (a) to (d):

(a) a differential thermal analysis profile having at least one endothermic peak in each of the ranges of 160° C. to 170° C., 215° C. to 225° C., and 260° C. to 270° C.;

(b) differential thermal analysis (DTA) and thermogravimetry (TG) profiles represented by FIGS. 5(*a*)-5(*b*);

(c) a Fourier-transform infrared absorption spectrum pattern represented by FIG. 6; and (d) a Fourier-transform infrared absorption spectrum pattern showing absorption bands and their intensities described in Table A, shown in FIG. 7.

[9] a method for producing Form II crystals of compound I comprising a peak at a diffraction angle (2θ) of 22.3±0.2(°) or 23.2±0.2(°) in powder x-ray diffraction obtained using Cu-Kα rays, the method comprising the steps of (a) converting compound I to an amorphous or low crystalline solid; and (b) exposing the amorphous or low crystalline solid to solvent vapor;

[10] the method according to [9], wherein step (a) comprises preparing the amorphous or low crystalline solid by the pulverization, melting and cooling, freeze drying, or spray drying of compound I;

[11] the method according to [9], wherein step (a) comprises preparing the amorphous or low crystalline solid by the freeze drying of compound I;

[12] the method according to [9], wherein step (a) comprises preparing the amorphous or low crystalline solid by the dissolution of compound I in water, dioxane, aqueous dioxane, or dimethyl sulfoxide followed by freeze drying;

[13] the method according to [9], wherein step (a) comprises preparing the amorphous or low crystalline solid by the dissolution of compound I in aqueous dioxane followed by freeze drying;

[14] the method according to [9], wherein the solvent used in the vapor exposure in step (b) is anisole, acetone, 2-butanone, toluene, acetonitrile, dimethoxyethane, or dimethoxymethane;

[15] the method according to [9], wherein the vapor exposure temperature in step (b) is 0° C. to 50° C.;

[16] the method according to [9], wherein the vapor exposure time in step (b) is 1 day to 10 days;

[17] the method according to [9], wherein the compound I in step (a) is Form I crystals of compound I;

[18] the method according to [9], wherein the Form II crystals comprise peaks at diffraction angles (2θ) of 22.3±0.2(°) and 23.2±0.2(°) in powder x-ray diffraction obtained using Cu-Kα rays;

[19] the method according to [9], wherein the Form II crystals further comprise a peak at a diffraction angle (2θ) of 21.5±0.2 or 22.0±0.2(°) in powder x-ray diffraction obtained using Cu-Kα rays;

[20] the method according to [9], wherein the Form II crystals comprise peaks at diffraction angles (2θ) of 13.9±0.2, 14.2±0.2, 15.8±0.2, 16.2±0.2, 18.2±0.2, 21.5±0.2, 22.0±0.2, 22.3±0.2, 23.2±0.2, and 24.3±0.2(°) in powder x-ray diffraction obtained using Cu-Kα rays;

[21] the method according to [9], wherein the Form II crystals exhibit a pattern represented by (2) of FIG. 1(*a*) or FIG. 3 in the powder x-ray diffraction obtained using Cu-Kα rays;

[22] the method according to [9], wherein the Form II crystals exhibit a differential thermal analysis (DTA) profile having at least one endothermic peak in any one of the ranges of 160° C. to 170° C. and 215° C. to 225° C.;

[23] the method according to [9], wherein the Form II crystals comprise any one absorption band selected from the group consisting of 3313±5, 839±1, and 828±1 (cm$^{-1}$) in a Fourier-transform infrared absorption spectrum pattern;

[24] the method according to [9], wherein the Form II crystals have at least one feature selected from the group consisting of the following (a) to (d):

(a) a differential thermal analysis (DTA) profile having at least one endothermic peak in each of the ranges of 160° C. to 170° C., 215° C. to 225° C., and 260° C. to 270° C.;

(b) differential thermal analysis (DTA) and thermogravimetry (TG) profiles represented by FIGS. 5(*a*)-5(*b*);

(c) a Fourier-transform infrared absorption spectrum pattern represented by FIG. 6; and (d) a Fourier-transform infrared absorption spectrum pattern showing absorption bands and their intensities described in the aforementioned table A;

[25] Form II crystals of compound I obtained by a method according to any one of [9] to [24];

[26] a pharmaceutical drug containing Form II crystals of compound I according to any one of [1] to [8] or [25] or Form II crystals of compound I obtained by a method according to any one of [9] to [24];

[27] the pharmaceutical drug according to [26], wherein the pharmaceutical drug is an activated blood coagulation factor X inhibitor:

[28] the pharmaceutical drug according to [27], wherein the pharmaceutical drug is an agent for preventing and/or treating thrombus or embolism;

[29] the pharmaceutical drug according to [28], wherein the pharmaceutical drug is an agent for preventing and/or treating cerebral infarction, cerebral embolism, pulmonary infarction, pulmonary embolism, myocardial infarction, angina pectoris, acute coronary syndrome, thrombus and/or embolism accompanying nonvalvular atrial fibrillation (NVAF), deep vein thrombosis, deep vein thrombosis after surgery, thrombosis after prosthetic valve/joint replacement, thromboembolism after total hip replacement (THR), thromboembolism after total knee replacement (TKR), thromboembolism after hip fracture surgery (HFS), thrombosis and/or reocclusion after revascularization, Buerger's disease, disseminated intravascular coagulation syndrome, systemic inflammatory response syndrome (SIRS), multiple organ dysfunction syndrome (MODS), thrombosis at the time of extracorporeal circulation, or blood coagulation at the time of blood collection;

[30] a pharmaceutical composition comprising Form II crystals of compound I according to any one of [1] to [8] or [25]

or Form II crystals of compound I obtained by a method according to any one of [9] to [24], and a pharmaceutically acceptable carrier; and

[31] a pharmaceutical composition comprising compound I, wherein the pharmaceutical composition comprises Form II crystals of compound I according to any one of [1] to [8] or [25] or Form II crystals of compound I obtained by a method according to any one of [9] to [24], in an amount of 0.01 wt. % to 99.9 wt. % with respect to the total weight of compound I in the pharmaceutical composition.

Advantageous Effects of the Invention

The present invention provides a novel crystal form of compound I and a method for producing the same.

BRIEF DESCRIPTION OF THE DRAWINGS

FIG. 4 shows the characteristic peaks (2θ(°)), d value (A), and relative intensity (%) in the powder x-ray diffraction of Form II crystals obtained in Example 4.

FIG. 7 shows characteristic absorption bands and their assignments and intensities in the infrared absorption spectrum of Form II crystals obtained in Example 4.

DETAILED DESCRIPTION

Hereinafter, the present invention will be described in detail.

$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide represented by the following formula (II) (hereinafter, also referred to as compound II):

[Formula 2]

(II)

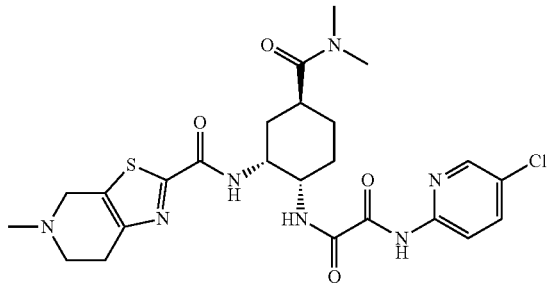

is a free form of compound I and is called edoxaban (N-(5-chloropyridin-2-yl)-N'-[(1S,2R,4S)-4-(N,N-dimethylcarbamoyl)-2-(5-methyl-4,5,6,7-tetrahydro[1,3]thiazolo[5,4-c]

pyridine-2-carboxamido)cyclohexyl]oxamide) as International Nonproprietary Name (INN).

No particular limitation is imposed on a method for producing compound II, and compound II can be produced by, for example, a method described in Patent Documents 1 to 9 or a method equivalent thereto.

Compound I is called edoxaban tosilate hydrate (written in English) as Japanese Accepted Names for Pharmaceuticals (JAN).

Figure 10:
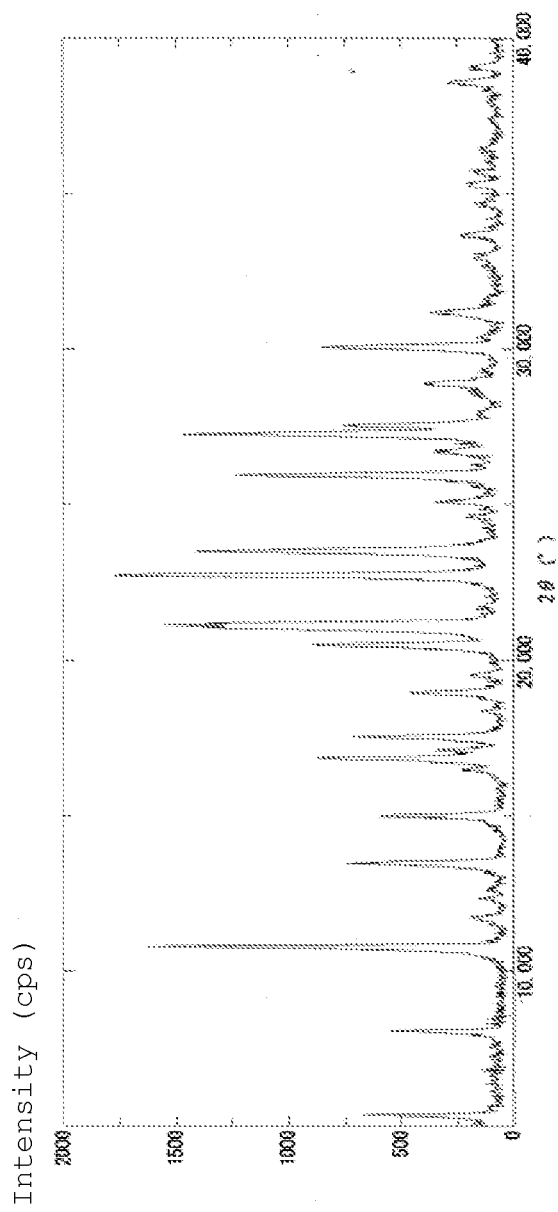
FIG. 10 shows the powder x-ray diffraction pattern of Form I crystals obtained in Example 2. The vertical axis shows intensity (cps), and the horizontal axis shows diffraction angle (2θ(°)).
Figure 11:
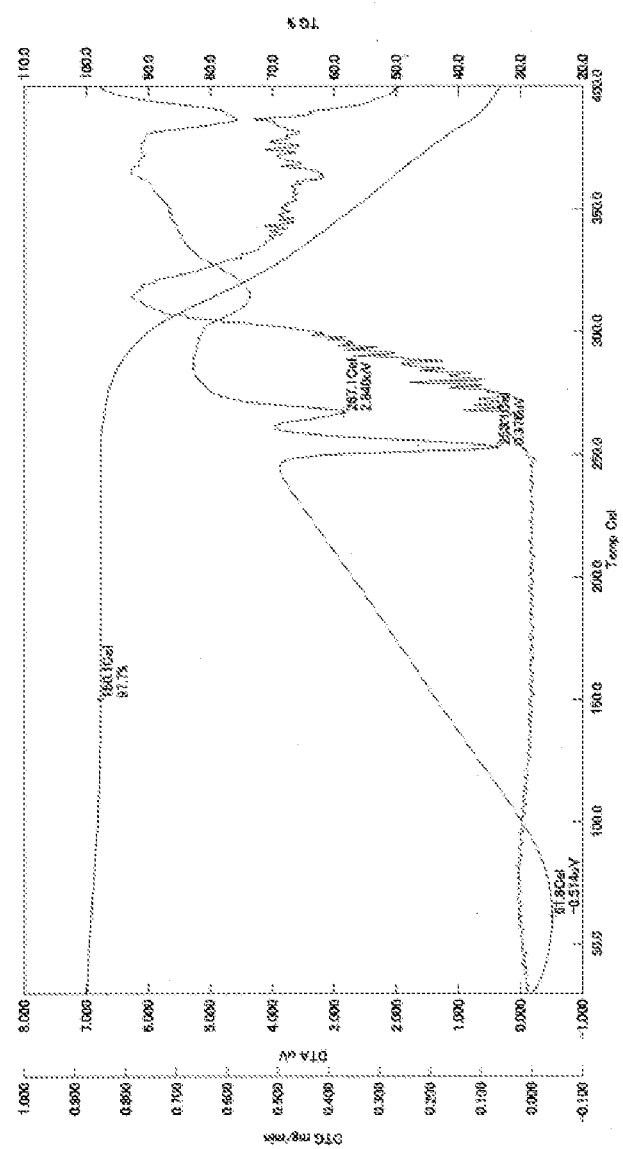
FIG. 11 shows the DTA profile and TG profile of Form I crystals obtained in Example 2. The vertical axis shows heat flow (μV) and change in weight (%), and the horizontal axis shows temperature (° C.).
Figure 12:
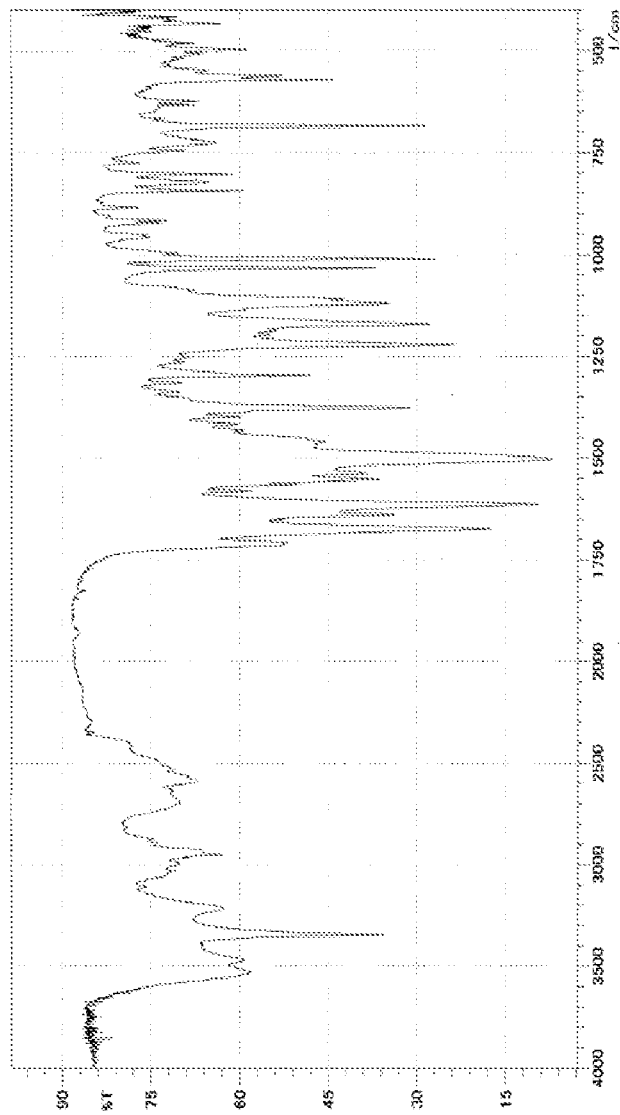
FIG. 12 shows the infrared absorption spectrum pattern of Form I crystals of compound I obtained in Example 2. The vertical axis shows transmittance (%), and the horizontal axis shows wavenumber ($cm^{-1}$).

No particular limitation is imposed on the method for producing compound I, and compound I can be produced by, for example, a method described in Patent Documents 1 to 9 or a method equivalent thereto, for example, involving adding a solution of p-toluenesulfonic acid in ethanol to compound II, then dissolving compound II by the addition of additional aqueous ethanol, and depositing crystals by the cooling of the reaction solution to obtain a crystalline compound. The crystals of compound I thus synthesized exhibit a powder x-ray diffraction pattern represented by FIG. 10 as a diffraction angle ($2\theta(°)$) in powder x-ray diffraction obtained using Cu-Kα rays and have characteristic peaks at diffraction angles ($2\theta(°)$) of 5.38±0.2, 8.08±0.2, 10.8±0.2, 13.5±0.2, 15.0±0.2, 16.9±0.2, 17.6±0.2, 20.5±0.2, 21.1±0.2, 22.7±0.2, 23.5±0.2, 26.0±0.2, 27.3±0.2, 27.6±0.2, and 30.0±0.2(°). In the present specification, the crystals of compound I that are produced by a method described in Patent Documents 1 to 9 or a method equivalent thereto and exhibit a powder x-ray diffraction pattern represented by FIG. 10 are also referred to as "Form I crystals of compound I" or "Form I crystals". The terms "Form I crystals of compound I" and "Form I crystals" are interchangeably used in the present specification. The Form I crystals of compound I further have any feature selected from the group consisting of the following (v) to (z):

(v) a DTA profile having two endothermic peaks at approximately 250° C. to approximately 270° C.;

(w) a DTA profile represented by FIG. 11;

(x) an infrared absorption spectrum comprising any one absorption band selected from the group consisting of 3344±5, 1675±2, 1614±2, 1503±2, 1222±1, 1171±1, 1033±1, 1012±1, 843±1, 825±1, and 802±1 ($cm^{-1}$);

(y) an infrared absorption spectrum pattern represented by FIG. 12; and/or (z) a melting point (decomp.) of approximately 246° C. to approximately 250° C.

In the present specification, the "amorphous solid" refers to a noncrystalline solid having no regular three-dimensional crystal structure. The compound of interest is confirmed to be amorphous, for example, when a broad powder x-ray diffraction profile (halo) without particular peaks is generated in the powder x-ray diffraction analysis of the compound.

In the present specification, the "low crystalline solid" means metastable crystals with low crystallinity that do not exhibit a powder x-ray diffraction profile as broad as that of the amorphous solid, but exhibit weak peaks in powder x-ray diffraction.

In the present specification, the "amorphous solid" and the "low crystalline solid" are also collectively referred to as an amorphous solid, etc.

One embodiment of the present invention relates to Form II crystals of compound I.

Figure 1A:
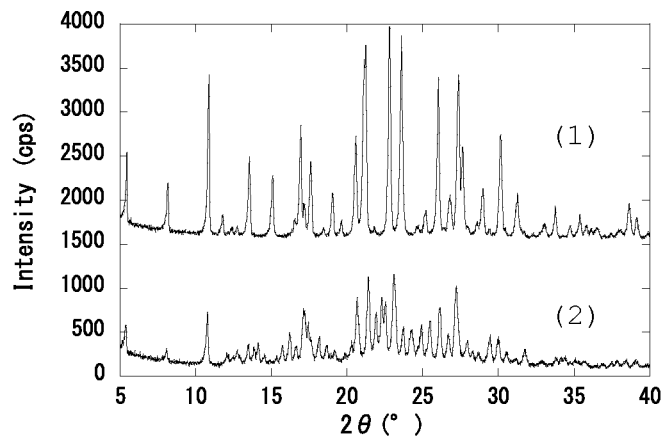
FIG. 1(a) shows the powder x-ray diffraction pattern of compound I obtained by the freeze drying-solvent vapor exposure method in Example 3(4), where the solvent in the vapor exposure is acetonitrile. The vertical axis shows intensity (cps), and the horizontal axis shows diffraction angle (2θ(°)). Line (1) shows the powder x-ray diffraction pattern of the starting substance (Form I crystals) before freeze drying, and line (2) shows the powder x-ray diffraction pattern of the substance obtained after freeze drying-solvent vapor exposure.
Figure 1B:
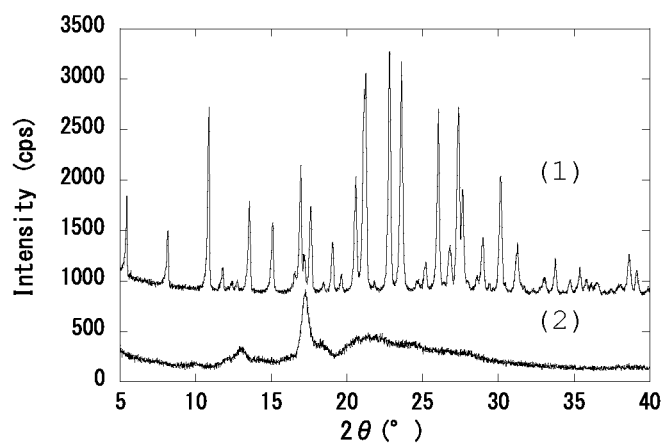
FIG. 1b shows the powder x-ray diffraction pattern of compound I obtained by the freeze drying-solvent vapor exposure method in Example 3(4), where the solvent in the vapor exposure is water. The vertical axis shows intensity (cps), and the horizontal axis shows diffraction angle (2θ(°)). Line (1) shows the powder x-ray diffraction pattern of the starting substance (Form I crystals) before freeze drying, and line (2) shows the powder x-ray diffraction pattern of the substance obtained after freeze drying-solvent vapor exposure.
Figure 1C:
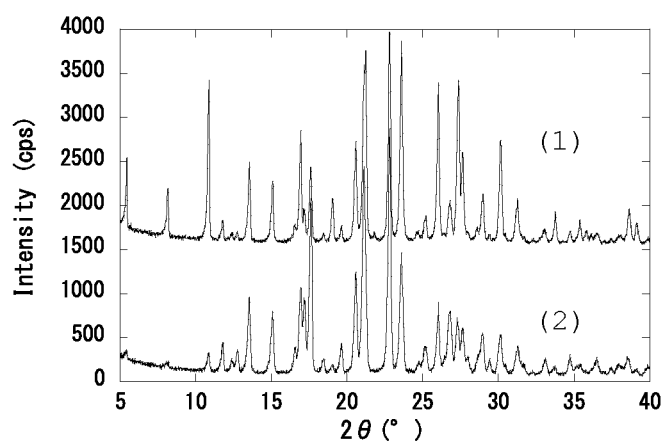
FIG. 1c shows the powder x-ray diffraction pattern of compound I obtained by the freeze drying-solvent vapor exposure method in Example 3(4), where the solvent in the vapor exposure is ethanol. The vertical axis shows intensity (cps), and the horizontal axis shows diffraction angle (2θ(°)). Line (1) shows the powder x-ray diffraction pattern of the starting substance (Form I crystals) before freeze drying, and line (2) shows the powder x-ray diffraction pattern of the substance obtained after freeze drying-solvent vapor exposure.
Figures 2, 3:
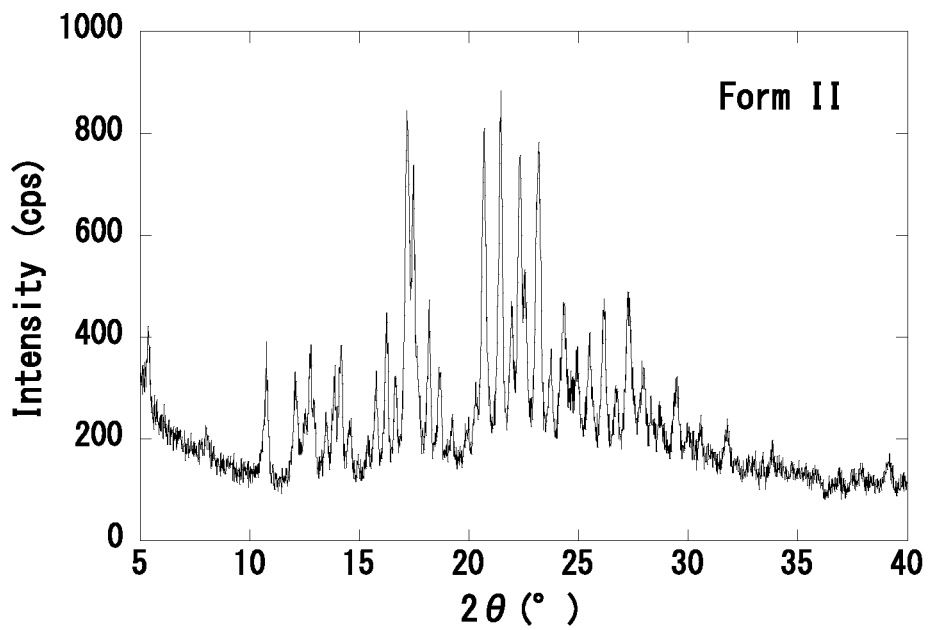
FIG. 2 shows summarized results of determining the ratio of the maximum diffraction line to the coefficient of background around 2θ=10° (S/B ratio) for the substance obtained by the freeze drying-solvent vapor exposure method in Example 3(4), and the crystal form of the substance.
FIG. 3 shows the powder x-ray diffraction pattern of Form II crystals obtained in Example 4. The vertical axis shows intensity (cps), and the horizontal axis shows diffraction angle (2θ(°)).

Results of powder x-ray diffraction analysis obtained using Cu-Kα rays on the Form II crystals of the present invention are shown in (2) of FIG. 1(*a*), FIG. 3, or FIG. 4. In the present specification, the value of powder x-ray diffraction analysis is a value obtained using Cu-Kα rays, unless otherwise specified. When x-rays other than Cu-Kα rays are used, $2\theta(°)$ varies according to the formula $2d \sin \theta = n\lambda$ (d represents the spacing between two planes; n represents any integer; λ represents the wavelength of x rays). However, these are merely indicated by another method substantially equivalent to the Form II crystals of the present invention and included in the scope of the present invention. This can be readily understood by those skilled in crystallography. Also, the relative intensities of peaks shown in these charts may vary depending on, for example, the degree of crystallinity of a sample or a preparation method. $2\theta(°)$ is substantially invariable, but may vary within an error range (generally, ±0.2°) recognized by those skilled in crystallography.

One embodiment of the present invention relates to Form II crystals of compound I comprising a peak at a diffraction angle ($2\theta(°)$) of 22.3±0.2(°) in powder x-ray diffraction obtained using Cu-Kα rays. Another embodiment of the present invention relates to Form II crystals of compound I comprising a peak at a diffraction angle ($2\theta(°)$) of 23.2±0.2(°) in powder x-ray diffraction obtained using Cu-Kα rays. A further embodiment of the present invention relates to the Form II crystals of compound I comprising peaks at diffraction angles ($2\theta(°)$) of 22.3±0.2(°) and 23.2±0.2(°) in powder x-ray diffraction obtained using Cu-Kα rays. A further embodiment of the present invention relates to the Form II crystals of compound I comprising a peak at a diffraction angle ($2\theta(°)$) of 22.3±0.2(°) or 23.2±0.2(°) in powder x-ray diffraction obtained using Cu-Kα rays and further comprising a peak at a diffraction angle ($2\theta(°)$) of 21.5±0.2 or 22.0±0.2(°) therein. Moreover, a further embodiment of the present invention relates to the Form II crystals of compound I comprising peaks at diffraction angles ($2\theta(°)$) of 13.9°, 14.2°, 15.8°, 16.2°, 18.2°, 21.5°, 22.0°, 22.3°, 23.2°, and 24.3° in powder x-ray diffraction obtained using Cu-Kα rays.

The Form II crystals of compound I of the present invention are preferably crystals comprising a peak at a diffraction angle ($2\theta(°)$) of 22.3±0.2(°) or 23.2±0.2(°) in powder x-ray diffraction obtained using Cu-Kα rays, more preferably crystals comprising at least two peaks selected from the group consisting of peaks at 21.5±0.2, 22.0±0.2, 22.3±0.2, and 23.2±0.2(°). Moreover, the Form II crystals of compound I of the present invention are preferably crystals having a chart or peaks represented by (2) of FIG. 1(*a*), FIG. 3, or FIG. 4 as diffraction angles ($2\theta(°)$) in powder x-ray diffraction obtained using Cu-Kα rays. These peaks are particularly useful in the discrimination between the Form II crystals and Form I crystals of compound I.

The compound can be determined to be crystalline from results of powder x-ray diffraction. For example, sharp peaks shown in (1) of FIG. 1(*a*), (2) of FIG. 1(*a*), (1) of FIG. 1(*b*), and (1) of FIG. 1(*c*) can demonstrate that the compound is crystalline. By contrast, a broad pattern except for a peak around 2θ=17.5 shown in (2) of FIG. 1(*b*) can demonstrate that the compound is low crystalline. The Form II crystals exhibit a smaller signal/background ratio (S/B ratio) in the powder x-ray diffraction pattern than that of Form I crystals, suggesting that the Form II crystals are lower crystalline than the Form I crystals. In the analysis of crystals using powder x-ray diffraction, if two or more polymorphs are contained in a sample, a crystal form having a smaller signal/background ratio may be hidden by the peak of a crystal form having a larger signal/background ratio and thus difficult to detect in terms of the properties of powder x-ray diffraction analysis.

Figure 5A:
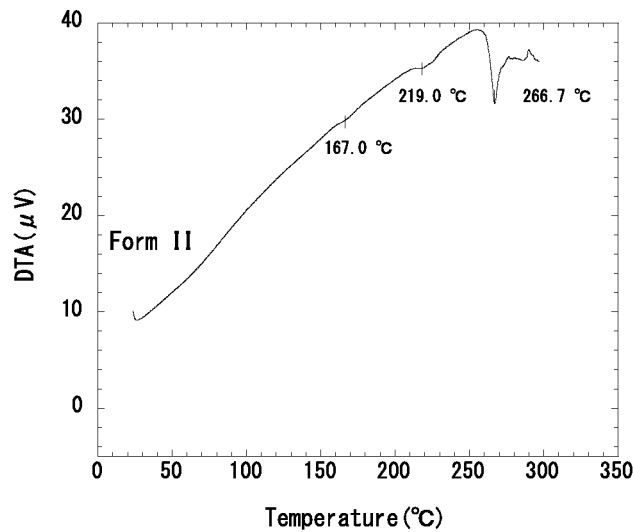
FIG. 5(a) shows the DTA profile of Form II crystals obtained in Example 4. In the DTA diagram, the vertical axis shows heat flow (μV), and the horizontal axis shows temperature (° C.). In the TG diagram, the vertical axis shows change in weight (%), and the horizontal axis shows temperature (° C.).
Figure 5B:
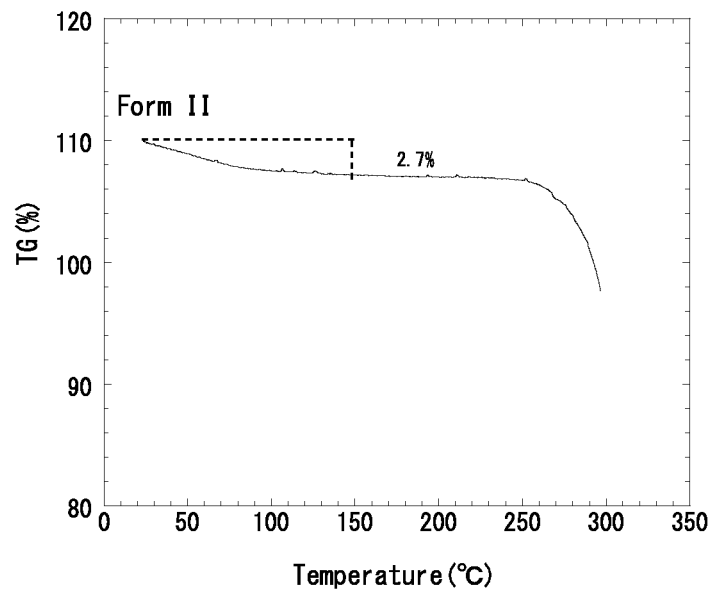
FIG. 5(b) shows the TG profile of Form II crystals obtained in Example 4. In the DTA diagram, the vertical axis shows heat flow (μV), and the horizontal axis shows temperature (° C.). In the TG diagram, the vertical axis shows change in weight (%), and the horizontal axis shows temperature (° C.).

Results of differential thermal analysis (DTA) and thermogravimetry (TG) on the Form II crystals of compound I of the present invention are shown in FIGS. 5(*a*)-5(*b*). One embodiment of the present invention relates to the Form II crystals of compound I that exhibit a DTA profile having at least one endothermic peak at approximately 160° C. to approximately 170° C. or exhibit a DTA profile having at least one endothermic peak at approximately 215° C. to approximately 225° C. Another embodiment of the present invention relates to the Form II crystals of compound I that exhibit a DTA profile having at least one endothermic peak in each of the ranges of approximately 160° C. to approximately 170° C., approximately 215° C. to approximately 225° C., and approximately 260° C. to approximately 270° C. or exhibit DTA and TG profiles represented by FIG. 5(a)-5(b). The Form II crystals of the present invention preferably exhibit a DTA profile having at least one endothermic peak at approximately 160° C. to approximately 170° C. or approximately 215° C. to approximately 225° C.

Figure 6:
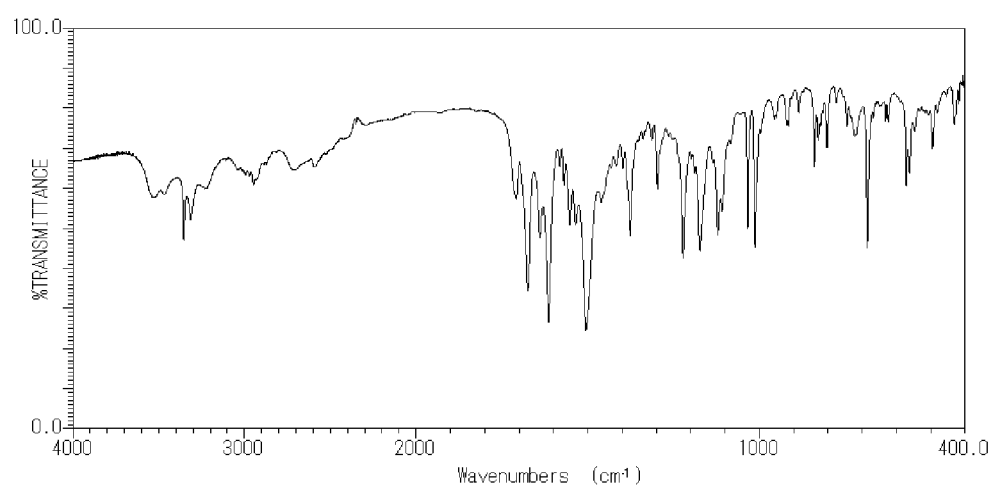
FIG. 6 shows the infrared absorption spectrum pattern of Form II crystals obtained in Example 4. The vertical axis shows transmittance (%), and the horizontal axis shows wavenumber ($cm^{-1}$).

The Fourier-transform infrared (FT-IR) absorption spectrum pattern of the compound of the present invention is shown in FIG. 6 and Table A (FIG. 7). In the present specification, the infrared absorption spectrum was measured by Fourier-transform infrared spectroscopy, unless otherwise specified. Each absorption band in the infrared absorption spectrum pattern is substantially invariable from the value described in the present specification, so long as it is measured using the same type of infrared spectroscopy. In this context, the term "substantially invariable" means that each peak in the infrared absorption spectrum may vary within an error range recognized by those skilled in crystallography (see e.g., Instruction Manual of the Japanese Pharmacopoeia, 15th ed., 2006, B-211 to B-217).

One embodiment of the present invention relates to the Form II crystals of compound I having an absorption band of 3313±5 (cm$^{-1}$) in a Fourier-transform infrared absorption spectrum. Another embodiment of the present invention relates to the Form II crystals of compound I having an absorption band of 3354±5 (cm$^{-1}$) in a Fourier-transform infrared absorption spectrum. One embodiment of the present invention relates to the Form II crystals of compound I having an absorption band of 839±1 (cm$^{-1}$) in a Fourier-transform infrared absorption spectrum. One embodiment of the present invention relates to the Form II crystals of compound I having an absorption band of 828±1 (cm$^{-1}$) in a Fourier-transform infrared absorption spectrum. The Form II crystals of compound I of the present invention preferably comprise any one absorption band selected from the group consisting of 3313±5, 828±1, and 839±1 (cm$^{-1}$).

More preferably, the Form II crystals of compound I of the present invention have, in addition to the aforementioned features of the powder x-ray diffraction patterns, any one feature selected from the group consisting of the following:
(a) a DTA profile having at least one endothermic peak in each of the ranges of 160° C. to 170° C., 215° C. to 225° C., and 260° C. to 270° C.;
(b) DTA and TG profiles represented by FIGS. 5(a)-5(b);
(c) a Fourier-transform infrared absorption spectrum pattern represented by FIG. 6; and
(d) a Fourier-transform infrared absorption spectrum pattern showing absorption bands and their intensities described in the aforementioned table A (FIG. 7).

One embodiment of the present invention relates to a method for producing the Form II crystals of compound I. This method comprises the steps of (a) converting compound I to an amorphous or low crystalline solid and (b) exposing the amorphous or low crystalline solid to solvent vapor. No particular limitation is imposed on the crystalline state of compound I used as a starting material in step (a), so long as it is compound I. Examples thereof include Form I crystals, a mixture of Form I crystals and an amorphous or low crystal solid of compound I, Form I crystals containing Form II crystals as impurities, compound I whose crystalline state is unconfirmed, compound I in a form other than Form I crystals or Form II crystals, and Form I crystals containing compound I in a form other than Form I crystals or Form II crystals as impurities. The compound I used as a starting material in step (a) is preferably Form I crystals of compound I.

Examples of preparation methods for the amorphous solid, etc. of compound I include, but are not limited to, the pulverization of compound I, the melting and cooling thereof, the freeze drying thereof, and the spray drying thereof and preferably include the melting and cooling method and the freeze drying method, with the freeze drying method being more preferable.

When compound I is converted to the amorphous solid, etc. by the dissolution of compound I in a solvent followed by freeze drying, examples of the solvent include, but are not particularly limited to, water, dioxane, aqueous dioxane, dimethyl sulfoxide, a dioxane/dimethyl sulfoxide mixed solution, a water/dioxane/dimethyl sulfoxide mixed solution, methanol, acetonitrile, tetrahydrofuran, aqueous tetrahydrofuran, dimethylformamide, and dimethylacetamide and preferably include 1,4-dioxane, aqueous 1,4-dioxane, a 1,4-dioxane/dimethyl sulfoxide mixed solution, and a water/1,4-dioxane/dimethyl sulfoxide mixed solution, with aqueous 1,4-dioxane being more preferable. In the case where the solvent is an aqueous solvent, no particular limitation is imposed on its percentage water content. Examples thereof include solvents having a percentage water content of 5%, 10%, 20%, 30%, 40%, 50%, 60%, 70%, 80%, 90%, or 95% and preferably include solvents having a percentage water content of 30%, 40%, 50%, 60%, or 70%, with solvents having a percentage water content of 40%, 50%, or 60% being more preferable. The amount of the solvent is not particularly limited and is, for example, 100 mL to 500 mL per g of the compound, preferably 200 mL to 400 mL per g of the compound. The freeze drying temperature and time are not particularly limited, and the freeze drying can be achieved, for example, at −80° C. to 30° C. over several hours to 24 hours.

The amorphous or low crystalline solid of compound I thus obtained can be exposed to solvent vapor to thereby prepare Form II crystals of compound I. The Form II crystals can be prepared by the exposure of the amorphous solid, etc. of compound I to solvent vapor, for example, through the following procedures: a first container (preferably a hermetic container) and a second container that is smaller than the first container and is capable of being housed in the first container are initially prepared. The exposure solvent is placed in the first container and the amorphous solid, etc. of compound I is placed in the second container, respectively, and left until they reach the exposure temperature condition. At the point in time when each container reaches the exposure temperature condition, the second container is placed in the first container without being hermetically sealed. The first container is hermetically sealed with a lid, a paraffin film, or the like wherein the second container is in the first container. The amorphous solid, etc. is exposed to the solvent at the temperature of interest for the time of interest. Then, the first container is unsealed, and crystals in the second container can be collected to obtain Form II crystals of compound I. In this context, examples of the types of the first and second containers include, but are not particularly limited to, beakers and vials. The types of the first and second containers may be selected appropriately according to the amount of the Form II crystals of compound I to be prepared. Likewise, examples of materials for the first and second containers include, but are not particularly limited to, glass or metal containers. These materials may be selected appropriately by those skilled in the art.

The solvent vapor exposure temperature is not particularly limited and is, for example, 0° C. to 50° C., preferably 5° C. to 40° C., more preferably 5° C., 25° C., or 40° C., even more preferably 5° C.

The solvent vapor exposure time is not particularly limited and may be adjusted appropriately according to the exposure temperature. The exposure time is usually 1 day to 10 days, preferably 2 days to 5 days, more preferably 3 days, 4 days, or 5 days.

The amount of the solvent placed in the first container is not particularly limited and is usually an amount in which the whole bottom of the first container is covered by an amount that reaches approximately 1 cm below the mouth of the second container, preferably an amount that reaches 1 cm in depth from the bottom of the first container.

Examples of the solvent used in the vapor exposure include water, acetone, anisole, 1-butanol, 2-butanol, tert-butyl methyl ether, cumene, ethyl acetate, diethyl ether, isopropyl acetate, methyl acetate, methyl ethyl ketone (2-butanone), 2-methyl-1-propanol, 1-propanol, 2-propanol, toluene, acetonitrile, dimethoxyethane, dimethoxymethane, and acetic acid. Preferable examples of the solvent used in the vapor exposure include anisole, acetone, 2-butanone, toluene, acetonitrile, dimethoxyethane, and dimethoxymethane, with acetone, acetonitrile, and dimethoxymethane being more preferable.

When acetonitrile is used as the solvent in the vapor exposure, its temperature is not particularly limited and is usually 0° C. to 50° C., preferably 5° C. to 40° C., more preferably 5° C., 25° C., or 40° C., even more preferably 5° C. Moreover, the amount of acetonitrile placed in the first container is not particularly limited and is usually an amount in which the whole bottom of the first container is covered by an amount that reaches approximately 1 cm below the mouth of the second container, preferably an amount that reaches 1 cm in depth from the bottom of the first container. The acetonitrile vapor exposure time is not particularly limited and is usually 2 days to 10 days, preferably 3 days, 4 days, or 5 days.

The obtained crystals can be examined for their physical properties using various instruments useful in crystal analysis including powder x-ray diffractometers and other instruments, for example, infrared spectrometers, thermal analyzers (e.g., differential thermal analyzers and thermogravimeters), and water vapor adsorption analyzers.

The thus-obtained Form II crystals of compound I of the present invention are useful as an activated blood coagulation factor X (also referred to as FXa) inhibitor, an anticoagulant agent, or an agent for preventing and/or treating thrombus or embolism. The Form II crystals of compound I of the present invention are useful as a pharmaceutical drug for mammals including humans, an activated blood coagulation factor X inhibitor, an anticoagulant agent, an agent for preventing and/or treating thrombosis and/or embolism, an agent for preventing and/or treating thrombotic diseases, and further, an agent for preventing (in the present specification, the prevention includes secondary prevention) and/or treating cerebral infarction, cerebral embolism, pulmonary infarction, pulmonary embolism, myocardial infarction, angina pectoris, acute coronary syndrome, thrombus and/or embolism accompanying nonvalvular atrial fibrillation (NVAF), deep vein thrombosis, deep vein thrombosis after surgery, thrombosis after prosthetic valve/joint replacement, thromboembolism after total hip replacement (THR), thromboembolism after total knee replacement (TKR), thromboembolism after hip fracture surgery (HFS), thrombosis and/or reocclusion after revascularization, Buerger's disease, disseminated intravascular coagulation syndrome, systemic inflammatory response syndrome (SIRS), multiple organ dysfunction syndrome (MODS), thrombosis at the time of extracorporeal circulation, or blood coagulation at the time of blood collection, or as bulk pharmaceuticals for these agents for preventing and/or treating the diseases.

A pharmaceutical drug comprising the Form II crystals of compound I of the present invention as an active ingredient is preferably provided in the form of a pharmaceutical composition comprising the Form II crystals of compound I of the present invention and one or two or more pharmaceutically acceptable carriers. No particular limitation is imposed on the dosage form of the pharmaceutical drug of the present invention, and the pharmaceutical drug of the present invention can be administered orally or parenterally and, preferably, administered orally.

The present invention also relates to a pharmaceutical composition comprising compound I. The pharmaceutical composition of the present invention comprises the Form II crystals of the present invention as at least a portion of compound I. The pharmaceutical composition may contain a crystal form (e.g., Form I crystals) other than Form II crystals as compound I. The proportion of the Form II crystals contained in the pharmaceutical composition can be in the range of 0.01 wt. % to 99.9 wt. %, for example, 0.01 wt. % or higher, 0.05 wt. % or higher, 0.1 wt. % or higher, 0.5 wt. % or higher, 1 wt. % or higher, 2 wt. % or higher, 3 wt. % or higher, 4 wt. % or higher, 5 wt. % or higher, 10 wt. % or higher, 20 wt. % or higher, 30 wt. % or higher, 40 wt. % or higher, 50 wt. % or higher, 60 wt. % or higher, 70 wt. % or higher, 80 wt. % or higher, 90 wt. % or higher, 95 wt. % or higher, 96 wt. % or higher, 97 wt. % or higher, 98 wt. % or higher, 99 wt. % or higher, 99.5 wt. % or higher, 99.6 wt. % or higher, 99.7 wt. % or higher, 99.8 wt. % or higher, or 99.9 wt. % or higher, with respect to the whole compound I in the pharmaceutical composition. The Form II crystals of compound I can be confirmed to be contained in the pharmaceutical composition by an instrumental analysis method (e.g., powder x-ray diffraction, thermal analysis, and infrared absorption spectroscopy) described in the present specification.

Examples of the pharmaceutically acceptable carriers used in the production of the pharmaceutical composition can include, but are not limited to, excipients, disintegrants or disintegration aids, binders, lubricants, coating agents, pigments, diluents, bases, solubilizers or solubilization aids, tonicity agents, pH adjusters, stabilizers, propellants, and tackiness agents.

Examples of preparations suitable for oral administration can include tablets, powders, granules, capsules, solutions, syrups, elixirs, and oily or aqueous suspensions. Moreover, examples of preparations suitable for parenteral administration can include injections, drops, suppositories, inhalants, and patches.

The dose of a pharmaceutical composition comprising the compound of the present invention or a pharmaceutically acceptable salt thereof, or a solvate thereof as an active ingredient is not particularly limited and can be selected appropriately according to various conditions such as the age, body weight, and symptoms of a patient. The pharmaceutical composition is preferably administered once to several times a day, preferably once to twice a day, at a dose of 1 mg to 1000 mg, preferably 5 mg to 500 mg, more preferably 5 mg to 300 mg, even more preferably 5 mg to 100 mg of the active ingredient per day in an adult according to the symptoms.

Hereinafter, Examples will be described. However, the present invention is not intended to be limited to them.

EXAMPLES

Example 1

Synthesis of $N^1$-(5-chloropyridin-2-yl)-$N^2$-((1S,2R, 4S)-4-[(dimethylamino)carbonyl]-2-{[(5-methyl-4,5, 6,7-tetrahydrothiazolo[5,4-c]pyridin-2-yl)carbonyl] amino}cyclohexyl)ethanediamide (Compound II)

Compound II was synthesized according to a method described in Patent Documents 1 to 9.

Example 2

Synthesis of Form I crystals of $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate monohydrate (Compound I)

4.1 g of the compound obtained in Example 1 was suspended in 50 mL of 15% aqueous ethanol at 60° C. The compound was dissolved by the addition of 7.42 mL of a 1 mol/L solution of p-toluenesulfonic acid in ethanol and then an additional 40 mL of 15% aqueous ethanol. Then, the solution was cooled to room temperature and stirred for 1 day. Deposited crystals were collected by filtration, washed with ethanol, and then dried under reduced pressure at room temperature for 2 hours to obtain 4.7 g of the title crystals (86%). Melting point (decomp.): 246 to 250° C.

Example 3

Search for Crystal Polymorph of Compound I

In this Example, powder x-ray diffractometry was performed under the following conditions: Source: Cu-Kα rays, filter: absent, detector: proportional counter, tube voltage: 40 kV, tube current: 50 mA, scan mode: continuous, scab rate: 0.015° 2θ/s, scan range: 2θ=5-40°, apparatus: X'pert MPD PW3040 (manufactured by PANalytical).

(1) Slurry Stirring Method

Approximately 100 mg of Form I crystals of compound I was weighed into each of 32 glass vials, and 1 mL each of 32 types of solvents (water, acetone, anisole, 1-butanol, 2-butanol, n-butyl acetate, t-butyl methyl ether, cumene, ethanol, ethyl acetate, diethyl ether, ethyl formate, heptane, isobutyl acetate, isopropyl acetate, methyl acetate, 3-methyl-1-butanol, methyl ethyl ketone (butanone), methyl isobutyl ketone (3-methyl-2-butanone), 2-methyl-1-propanol, pentane, 1-pentanol, 1-propanol, 2-propanol, propyl acetate, toluene, dichloromethane, acetonitrile, 1,4-dioxane, tetrahydrofuran, dimethoxyethane, and dimethoxymethane) was added thereto. The samples supplemented with diethyl ether or pentane were stirred at a constant temperature of 20° C. for 61 hours or longer. The samples supplemented with the other solvents were slurry-stirred at 50° C. for 50 hours and then cooled to 20° C.

Each sample thus slurry-stirred was centrifuged, and the supernatant was removed using a Pasteur pipette. The residual solvent was further removed on a filter paper, and the residue was then dried in air overnight.

All 32 types of crystals obtained using each solvent exhibited a powder x-ray diffraction pattern equivalent to Form I crystals before slurry stirring. Thus, the slurry stirring method failed to produce a new polymorph of compound I.

(2) Recrystallization Method Using Single Solvent 8 mL of methanol was added to approximately 500 g of Form I crystals of compound I, and the crystals were dissolved by heating in a hot bath (60° C.). Then, the solution was left at room temperature to deposit crystals. The obtained crystals were collected by filtration and dried in air overnight.

Recrystallization was attempted by the dissolution of Form I crystals of compound I by heating in the same way as in methanol except that the solvent was changed to water, ethanol, acetonitrile, dimethyl sulfoxide, or dimethylformamide.

When methanol, water, ethanol, acetonitrile, or dimethylformamide were used alone as a single solvent, crystals were deposited. However, all of these crystals exhibited a powder x-ray diffraction pattern equivalent to Form I crystals before recrystallization. Use of dimethyl sulfoxide as a single solvent failed to deposit solids.

(3) Recrystallization Method Using Aqueous Solvent 10 mL of 10% aqueous methanol was added to approximately 500 mg of Form I crystals of compound I, and the crystals were dissolved by heating in a hot bath (60° C.). The solution was thermally filtered. The filtrate was left at room temperature to deposit crystals. The obtained crystals were collected by filtration and dried in air overnight.

Recrystallization was attempted by the dissolution of Form I crystals of compound I by heating in the same way as when using 10% aqueous methanol as a solvent except that the solvent was changed to 20% aqueous methanol, 50% aqueous methanol, 80% aqueous methanol, 10% aqueous ethanol, 20% aqueous ethanol, 50% aqueous ethanol, 80% aqueous ethanol, 10% aqueous acetone, 20% aqueous acetone, 50% aqueous acetone, 80% aqueous acetone, 10% aqueous acetonitrile, 20% aqueous acetonitrile, 50% aqueous acetonitrile, 80% aqueous acetonitrile, 10% aqueous 1-propanol, 20% aqueous 1-propanol, 50% aqueous 1-propanol, 80% aqueous 1-propanol, 10% aqueous 2-propanol, 20% aqueous 2-propanol, 50% aqueous 2-propanol, or 80% aqueous 2-propanol.

When 24 types of solvents were used, crystals were deposited in all cases. However, all of these crystals exhibited a powder x-ray diffraction pattern equivalent to Form I crystals before recrystallization.

(4) Freeze Drying-Solvent Vapor Exposure Method 120 mL of water was mixed with 120 mL of 1,4-dioxane to prepare a water/1,4-dioxane (1:1) mixed solution. Approximately 500 mg of Form I crystals of compound I was dissolved by the addition of 200 mL of the water/1,4-dioxane (1:1) mixed solution, and the solution was divided into six 100-mL beakers and freeze-dried.

Each obtained freeze-dried cake was placed together with the beaker in a metal drum (Sanko Astec Inc., stainless container, 4 L, CTH-18) containing a small amount of each solvent for vapor exposure (water, ethanol, or acetonitrile). Two beakers were used in each solvent vapor exposure for reproducibility. The metal drum was stored in a refrigerator for 5 days, and the freeze-dried cake was then taken out of the container and dried overnight at normal pressure. The freeze-dried cake exposed to solvent vapor was gently mixed using a spatula.

FIG. 1 shows the powder x-ray diffraction pattern of compound I obtained by the freeze drying-solvent vapor exposure method. Reproducibility was obtained between two beakers in all solvent vapor exposure operations. FIG. 1 shows typical results of compound I obtained from any one of the beakers in each solvent vapor exposure.

The sample exposed to water vapor and the sample exposed to acetonitrile vapor exhibited a diffraction pattern different from that of Form I crystals (FIG. 1(a)).

FIG. 2 shows summarized results of determining the ratio of the maximum diffraction line to the coefficient of background around 2θ=10° (S/B ratio) for compound I obtained by the freeze drying-solvent vapor exposure method, the diffraction angle of the main diffraction line, and the crystal form of compound I.

The sample exposed to acetonitrile vapor exhibited distinct diffraction lines with an S/B ratio of 5 or larger and was thus determined to be crystalline. The sample exposed to acetonitrile vapor differed in both the diffraction angle of the main diffraction line and the diffraction pattern from Form I crystals and thus seemed to have a crystal form different from the form of Form I crystals (FIGS. 1(a) and 2).

The sample exposed to water vapor had an S/B ratio of 5 or larger, but exhibited diffraction lines as exceedingly few in number as two or three lines compared with usual crystalline samples and the very broad pattern of the diffraction lines and was thus determined to be low crystalline (FIGS. 1(b) and 2).

The sample exposed to ethanol vapor exhibited distinct diffraction lines with an S/B ratio of 5 or larger and was thus determined to be crystalline. The crystal form of the sample exposed to ethanol vapor had the diffraction angle of the main diffraction line and a diffraction pattern equivalent to Form I crystals and thus seemed to be Form I crystals (FIGS. 1(c) and 2).

Example 4

Form II Crystals of Compound I 2.5 g of Form I crystals of compound I was dissolved by the addition of 1000 mL of the water/1,4-dioxane (1:1) mixed solution, and approximately 80 mL/beaker of the solution was dispensed to fourteen 100-mL glass beakers and freeze-dried.

Each obtained freeze-dried cake was placed together with the beaker in a metal drum (Sanko Astec Inc., stainless container, 4 L, CTH-18) containing a small amount of acetonitrile and exposed to solvent vapor in a refrigerator (approximately 5° C.) for 8 days. The freeze-dried cake was taken out of the container and stored at room temperature for 6 days in a desiccator containing silica gel. The freeze-dried cakes exposed to solvent vapor were collected from the fourteen beakers and combined into one portion, which was then subjected to the following Test Examples 1 to 5.

Test Example 1

The Form II crystals obtained in Example 4 were prepared for analysis and analyzed for their crystal form using a powder x-ray diffractometer. Conditions for the powder x-ray diffractometry were the same as those in Example 3.

The results of the powder x-ray diffraction pattern are shown in FIG. 3, and characteristic peaks and their relative intensities are shown in FIG. 4.

Test Example 2

The Form II crystals obtained in Example 4 were prepared for analysis and assayed by thermal analysis (TG/DTA). Assay conditions for the thermal analysis (TG/DTA): atmosphere: 200 mL/min nitrogen, heating rate: 10° C./min, sample amount: approximately 3 mg, apparatus: TG/DTA6200 (manufactured by SII NanoTechnology Inc.).

The results are shown in FIGS. 5(a)-5(b). The crystals obtained in Example 4 exhibited a thermal analysis (DTA) profile having at least one endothermic peak in each of the ranges of approximately 160° C. to approximately 170° C., approximately 215° C. to approximately 225° C., and approximately 260° C. to approximately 270° C.

Test Example 3

The Form II crystals obtained in Example 4 were prepared for analysis and analyzed by infrared absorption spectroscopy. Conditions for the infrared absorption spectroscopy: method: KBr tablet method, apparatus: FT-720 (manufactured by HORIBA, Ltd.).

The results are shown in FIGS. 6 and 7. The crystals obtained in Example 4 exhibited an infrared absorption spectrum pattern having characteristic absorption bands around 3300 to 3400 ($cm^{-1}$) and around 900 to 700 ($cm^{-1}$).

Test Example 4

Approximately 20 mg of the Form II crystals obtained in Example 4 was analyzed for time-dependent change in weight in a relative humidity (RH) range of 10 to 90% using a water vapor adsorption analyzer (SGA-100, VTI Corporation).

Figure 8:
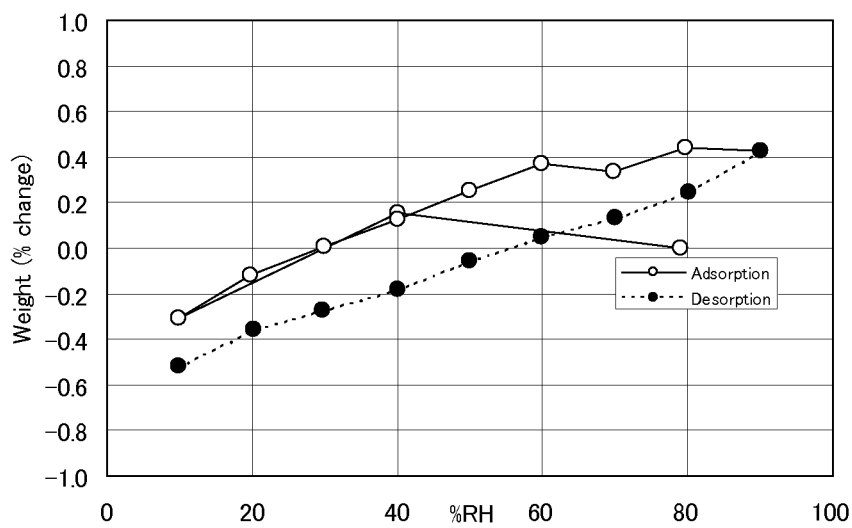
FIG. 8 shows the absorption and desorption behavior of Form II crystals obtained in Example 4. The vertical axis shows weight (% change), and the horizontal axis shows relative humidity (%).

The results are shown in FIG. 8.

Test Example 5

The Form II crystals obtained in Example 4 and Form I crystals of compound I were analyzed for their solubility in water and an acetate buffer (pH 4.5) at 37° C.

Figure 9:
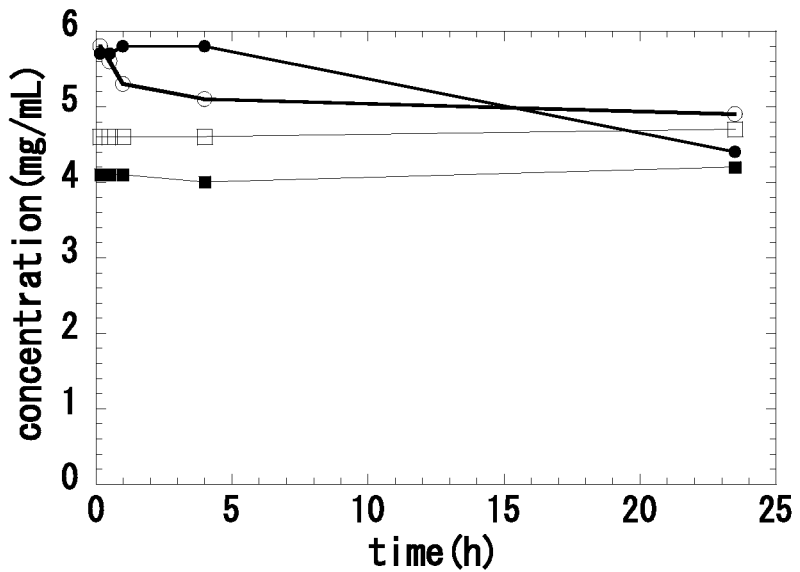
FIG. 9 shows the dissolution behavior in water (filled circle) or acetate buffer of pH 4.5 (open circle) of Form II crystals obtained in Example 4, and the dissolution behavior in water (filled square) or acetate buffer of pH 4.5 (open square) of Form I crystals. The vertical axis shows concentration (mg/mL), and the horizontal axis shows time (h) after dissolution in each solution.

The results are shown in FIG. 9.

Preparation Example

The Form II crystals (40.4 mg) of the compound, mannitol (99.2 mg), pregelatinized starch (42.0 mg), crospovidone (10.7 mg), hydroxypropyl cellulose (6.1 mg), and magnesium stearate (1.6 mg) are used to produce tablets according to a widely known method. The tablets can be coated, if necessary.

The invention claimed is:

1. Form II crystals of $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate monohydrate represented by the following formula (I):

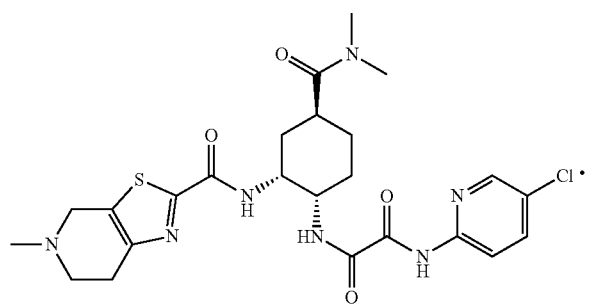

(b) differential thermal analysis and thermogravimetry profiles represented by FIGS. 5(*a*)-5(*b*);

(c) a Fourier-transform infrared absorption spectrum pattern represented in FIG. 6; and (d) a Fourier-transform infrared absorption spectrum pattern showing absorption bands and their intensities described in FIG. 7.

6. A method for producing Form II crystals of $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate monohydrate represented by the following formula (I):

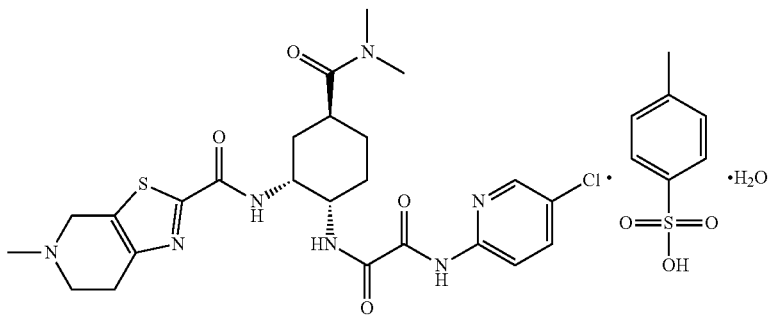

comprising peaks at diffraction angles (2θ) of 13.9±0.2, 14.2±0.2, 15.8±0.2, 16.2±0.2, 18.2±0.2, 21.5±0.2, 22.0±0.2, 22.3±0.2, 23.2±0.2, and 24.3±0.2(°) in powder x-ray diffraction obtained using Cu-Kα rays, the method comprising the steps of (a) converting a compound represented by formula (I) to an amorphous or low crystalline solid by the dissolution of the compound represented by formula (I) in water, dioxane, aqueous dioxane, or dimethyl sulfoxide followed by freeze drying; and (b) exposing the amorphous or low crystalline solid to solvent vapor.

7. The method according to claim 6, wherein step (a) comprises preparing the amorphous or low crystalline solid by the dissolution of the compound represented by formula (I) in aqueous dioxane followed by freeze drying.

8. The method according to claim 6, wherein the solvent used in the vapor exposure in step (b) is anisole, acetone, 2-butanone, toluene, acetonitrile, dimethoxyethane, or dimethoxymethane.

9. The method according to claim 6, wherein the vapor exposure temperature in step (b) is 0° C. to 50° C.

10. The method according to claim 6, wherein the vapor exposure time in step (b) is 1 day to 10 days.

11. The method according to claim 6, wherein the compound represented by formula (I) in step (a) is Form I crystals of the compound represented by formula (I).

12. The method according to claim 6, wherein the Form II crystals exhibit a pattern represented by line (2) in FIG. 1(*a*) or by Form II in FIG. 3 in the powder x-ray diffraction obtained using Cu-Kα rays.

13. The method according to claim 6, wherein the Form II crystals exhibit a differential thermal analysis profile having at least one endothermic peak in any one of the ranges of 160° C. to 170° C. and 215° C. to 225° C.

-continued

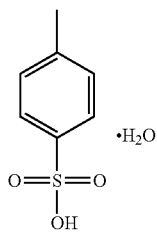

comprising peaks at diffraction angles (2θ) of 13.9±0.2, 14.2±0.2, 15.8±0.2, 16.2±0.2, 18.2±0.2, 21.5±0.2, 22.0±0.2, 22.3±0.2, 23.2±0.2, and 24.3±0.2(°) in powder x-ray diffraction obtained using Cu-Kα rays.

2. The crystals according to claim 1, wherein the powder x-ray diffraction obtained using Cu-Kα rays shows a pattern represented by line (2) in FIG. 1(*a*) or by Form II in FIG. 3.

3. The crystals according to claim 1, wherein the crystals exhibit a differential thermal analysis profile having at least one endothermic peak in any one of the ranges of 160° C. to 170° C. and 215° C. to 225° C.

4. The crystals according to claim 1, comprising any one absorption band selected from the group consisting of 3313±5, 839±1, and 828±1 (cm$^{-1}$) in a Fourier-transform infrared absorption spectrum.

5. The crystals according to claim 1, wherein the crystals have at least one feature selected from the group consisting of the following (a) to (d):

(a) a differential thermal analysis profile having at least one endothermic peak in each of the ranges of 160° C. to 170° C., 215° C. to 225° C., and 260° C. to 270° C.;

14. The method according to claim 6, wherein the Form II crystals comprise any one absorption band selected from the group consisting of 3313±5, 839±1, and 828±1 (cm$^{-1}$) in a Fourier-transform infrared absorption spectrum.

15. The method according to claim 6, wherein the Form II crystals have at least one feature selected from the group consisting of the following (a) to (d):
(a) a differential thermal analysis profile having at least one endothermic peak in each of the ranges of 160° C. to 170° C., 215° C. to 225° C., and 260° C. to 270° C.;
(b) differential thermal analysis and thermogravimetry profiles represented by FIGS. 5(a)-5(b);
(c) a Fourier-transform infrared absorption spectrum pattern represented by FIG. 6; and
(d) a Fourier-transform infrared absorption spectrum pattern showing absorption bands and their intensities described in FIG. 7.

16. Form II crystals of a compound represented by formula (I)

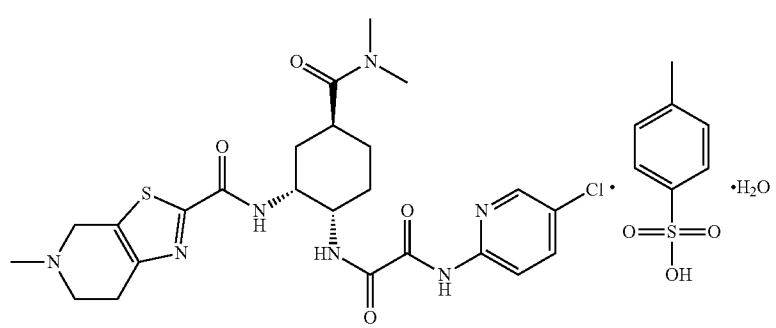

obtained by a method according to claim 6.

17. A pharmaceutical drug containing Form II crystals of a compound represented by formula (I)

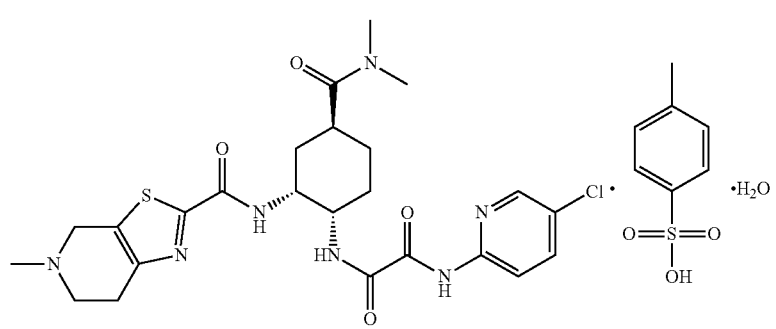

comprising peaks at diffraction angles (2θ) of 13.9±0.2, 14.2±0.2, 15.8±0.2, 16.2±0.2, 18.2±0.2, 21.5±0.2, 22.0±0.2, 22.3±0.2, 23.2±0.2, and 24.3±0.2(°) in powder x-ray diffraction obtained using Cu-Kα rays or Form II crystals of a compound represented by formula (I) obtained by a method according to claim 6.

18. The pharmaceutical drug according to claim 17, wherein the pharmaceutical drug is an activated blood coagulation factor X (FXa) inhibitor.

19. The pharmaceutical drug according to claim 18, wherein the pharmaceutical drug is an agent for treating thrombus or embolism.

20. The pharmaceutical drug according to claim 19, wherein the pharmaceutical drug is an agent for treating cerebral infarction, cerebral embolism, pulmonary infarction, pulmonary embolism, myocardial infarction, angina pectoris, acute coronary syndrome, thrombus and/or embolism accompanying nonvalvular atrial fibrillation, deep vein thrombosis, deep vein thrombosis after surgery, thrombosis after prosthetic valve/joint replacement, thromboembolism after total hip replacement, thromboembolism after total knee replacement, thromboembolism after hip fracture surgery, thrombosis and/or reocclusion after revascularization, Buerger's disease, disseminated intravascular coagulation syndrome, systemic inflammatory response syndrome, multiple organ dysfunction syndrome, thrombosis at the time of extracorporeal circulation, or blood coagulation at the time of blood collection.

21. A pharmaceutical composition comprising Form II crystals of a compound represented by formula (I)

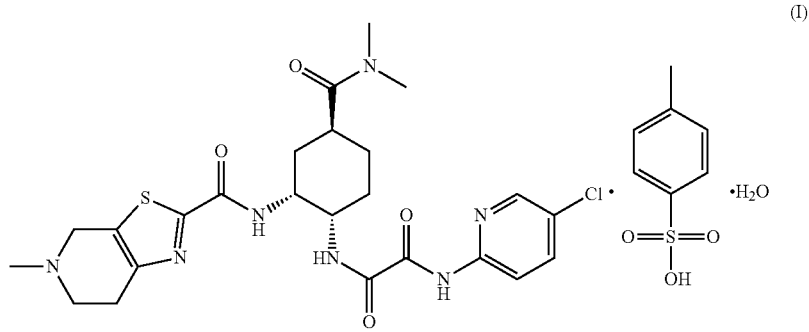

comprising peaks at diffraction angles (2θ) of 13.9±0.2, 14.2±0.2, 15.8±0.2, 16.2±0.2, 18.2±0.2, 21.5±0.2, 22.0±0.2, 22.3±0.2, 23.2±0.2, and 24.3±0.2(°) in powder x-ray diffraction obtained using Cu-Kα rays or Form II crystals of a compound represented by formula (I) obtained by a method according to claim 6, and a pharmaceutically acceptable carrier.

22. A pharmaceutical composition comprising a compound represented by formula (I)

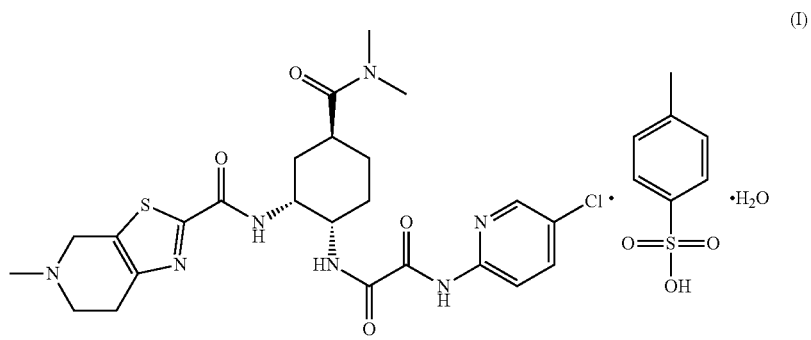

wherein the pharmaceutical composition comprises Form II crystals of a compound represented by formula (I) comprising peaks at diffraction angles (2θ) of 13.9±0.2, 14.2±0.2, 15.8±0.2, 16.2±0.2, 18.2±0.2, 21.5±0.2, 22.0±0.2, 22.3±0.2, 23.2±0.2, and 24.3±0.2(°) in powder x-ray diffraction obtained using Cu-Kα rays or Form II crystals of a compound represented by formula (I) obtained by a method according to claim 9, in an amount of 0.01 wt. % to 99.9 wt. % with respect to the total weight of compound I in the pharmaceutical composition.

* * * * *